(12) United States Patent
Liebing (10) Patent No.: US 8,932,141 B2
(45) Date of Patent: Jan. 13, 2015

(54) FLEXIBLE SHAFT ARRANGEMENT

(75) Inventor: Reiner Liebing, Potsdam (DE)

(73) Assignee: ECP Entwicklungsgesellschaft mbH, Berlin (DE)

( * ) Notice: Subject to any disclaimer, the term of this patent is extended or adjusted under 35 U.S.C. 154(b) by 0 days.

(21) Appl. No.: 13/261,257

(22) PCT Filed: Oct. 22, 2010

(86) PCT No.: PCT/EP2010/006528
§ 371 (c)(1),
(2), (4) Date: Jun. 21, 2012

(87) PCT Pub. No.: WO2011/047883
PCT Pub. Date: Apr. 28, 2011

(65) Prior Publication Data
US 2012/0264523 A1    Oct. 18, 2012

(30) Foreign Application Priority Data
Oct. 23, 2009  (EP) .................................... 09075474

(51) Int. Cl.
*F16C 1/06* (2006.01)
*B23P 17/00* (2006.01)
*A61M 1/12* (2006.01)
*F16C 41/00* (2006.01)
*A61M 1/10* (2006.01)

(52) U.S. Cl.
CPC .................. *F16C 1/06* (2013.01); *A61M 1/125* (2014.02); *F16C 41/008* (2013.01); *A61M 1/101* (2013.01)
USPC ................. 464/52; 464/60; 74/502.5; 72/368

(58) Field of Classification Search
USPC ............... 464/52, 57–60, 180–182; 74/502.5; 604/6.16, 8, 9, 508; 417/423.1, 423.14, 417/474–476; 72/368
See application file for complete search history.

(56) References Cited

U.S. PATENT DOCUMENTS

| 1,743,506 | A | * | 1/1930 | Watson et al. ........... 74/502.5 X |
| 3,242,691 | A | * | 3/1966 | Robinson et al. ........... 464/57 X |
| 3,510,229 | A | | 5/1970 | Smith et al. |
| 3,568,659 | A | | 3/1971 | Karnegis |
| 3,802,551 | A | | 4/1974 | Somers |
| 3,812,812 | A | | 5/1974 | Hurwitz |
| 4,014,317 | A | | 3/1977 | Bruno |
| 4,207,028 | A | | 6/1980 | Ridder |
| 4,424,045 | A | * | 1/1984 | Kulischenko et al. .......... 464/52 |
| 4,559,951 | A | | 12/1985 | Dahl et al. |
| 4,563,181 | A | | 1/1986 | Wijayarathna |
| 4,625,712 | A | * | 12/1986 | Wampler |
| 4,679,558 | A | | 7/1987 | Kensey et al. |

(Continued)

FOREIGN PATENT DOCUMENTS

| CA | 1008330 A1 | 4/1977 |
| CA | 2311977 A1 | 12/2000 |

(Continued)

*Primary Examiner* — Gregory Binda
*Assistant Examiner* — Josh Skroupa
(74) *Attorney, Agent, or Firm* — Marshall & Melhorn, LLC (57) ABSTRACT

A flexible shaft arrangement is provided having a ductile shaft, a sleeve which surrounds the shaft as well as a jacket which surrounds the shaft and the sleeve. The sleeve extends within the jacket at least sectionally in arcuate form and thus produces a contact of the shaft at the inner contour of the sleeve point-wise. Vibrations or knocks of the shaft are thus effectively damped.

13 Claims, 4 Drawing Sheets

(56) References Cited

U.S. PATENT DOCUMENTS

| | | |
|---|---|---|
| 4,686,982 A | 8/1987 | Nash |
| 4,747,821 A | 5/1988 | Kensey et al. |
| 4,749,376 A | 6/1988 | Kensey et al. |
| 4,753,221 A | 6/1988 | Kensey et al. |
| 4,801,243 A | 1/1989 | Norton |
| 4,817,613 A | 4/1989 | Jaraczewski et al. |
| 4,905,777 A * | 3/1990 | Spies ................ 464/57 X |
| 4,919,647 A | 4/1990 | Nash |
| 4,957,504 A | 9/1990 | Chardack |
| 4,969,865 A | 11/1990 | Hwang et al. |
| 4,979,939 A * | 12/1990 | Shiber |
| 4,995,857 A | 2/1991 | Arnold |
| 5,011,469 A | 4/1991 | Buckberg et al. |
| 5,035,055 A * | 7/1991 | McCullough |
| 5,040,944 A | 8/1991 | Cook |
| 5,042,984 A | 8/1991 | Kensey et al. |
| 5,052,404 A | 10/1991 | Hodgson |
| 5,061,256 A | 10/1991 | Wampler |
| 5,092,844 A | 3/1992 | Schwartz et al. |
| 5,097,849 A | 3/1992 | Kensey et al. |
| 5,108,411 A | 4/1992 | McKenzie |
| 5,112,292 A | 5/1992 | Hwang et al. |
| 5,113,872 A | 5/1992 | Jahrmarkt et al. |
| 5,117,838 A | 6/1992 | Palmer et al. |
| 5,118,264 A | 6/1992 | Smith |
| 5,129,861 A * | 7/1992 | Furukawa et al. ......... 464/52 X |
| 5,145,333 A | 9/1992 | Smith |
| 5,163,910 A | 11/1992 | Schwartz et al. |
| 5,169,378 A | 12/1992 | Figuera |
| 5,183,384 A | 2/1993 | Trumbly |
| 5,191,888 A | 3/1993 | Palmer et al. |
| 5,201,679 A | 4/1993 | Velte, Jr. et al. |
| 5,275,580 A | 1/1994 | Yamazaki |
| 5,315,892 A * | 5/1994 | Gabas et al. ............ 74/502.5 X |
| 5,373,619 A | 12/1994 | Fleischhacker et al. |
| 5,376,114 A | 12/1994 | Jarvik |
| 5,501,574 A | 3/1996 | Raible |
| 5,531,789 A | 7/1996 | Yamazaki et al. |
| 5,701,911 A | 12/1997 | Sasamine et al. |
| 5,755,784 A | 5/1998 | Jarvik |
| 5,776,190 A | 7/1998 | Jarvik |
| 5,813,405 A | 9/1998 | Montano, Jr. et al. |
| 5,820,571 A | 10/1998 | Erades et al. |
| 5,851,174 A | 12/1998 | Jarvik et al. |
| 5,882,329 A | 3/1999 | Patterson et al. |
| 5,888,241 A | 3/1999 | Jarvik |
| 5,938,672 A | 8/1999 | Nash |
| 6,030,397 A | 2/2000 | Monetti et al. |
| 6,129,704 A | 10/2000 | Forman et al. |
| 6,152,693 A | 11/2000 | Olsen et al. |
| 6,168,624 B1 | 1/2001 | Sudai |
| 6,254,359 B1 | 7/2001 | Aber |
| 6,302,910 B1 | 10/2001 | Yamazaki et al. |
| 6,308,632 B1 | 10/2001 | Shaffer |
| 6,336,939 B1 | 1/2002 | Yamazaki et al. |
| 6,346,120 B1 | 2/2002 | Yamazaki et al. |
| 6,387,125 B1 | 5/2002 | Yamazaki et al. |
| 6,503,224 B1 | 1/2003 | Forman et al. |
| 6,506,025 B1 | 1/2003 | Gharib |
| 6,508,787 B2 | 1/2003 | Erbel et al. |
| 6,517,315 B2 | 2/2003 | Belady |
| 6,527,521 B2 | 3/2003 | Noda |
| 6,533,716 B1 | 3/2003 | Scmitz-Rode et al. |
| 6,537,030 B1 | 3/2003 | Garrison |
| 6,537,315 B2 | 3/2003 | Yamazaki et al. |
| 6,592,612 B1 | 7/2003 | Samson et al. |
| 6,652,548 B2 | 11/2003 | Evans et al. |
| 6,685,696 B2 | 2/2004 | Fleischhacker et al. |
| 6,719,791 B1 | 4/2004 | Nusser |
| 6,860,713 B2 | 3/2005 | Hoover |
| 6,913,539 B1 * | 7/2005 | Scherer ................ 464/52 X |
| 6,945,977 B2 | 9/2005 | Demarais et al. |
| 6,981,942 B2 | 1/2006 | Khaw et al. |
| 7,022,100 B1 | 4/2006 | Aboul-Hosn et al. |
| 7,027,875 B2 | 4/2006 | Siess et al. |
| 7,074,018 B2 | 7/2006 | Chang |
| 7,179,273 B1 | 2/2007 | Palmer et al. |
| 7,393,181 B2 | 7/2008 | McBride et al. |
| 7,467,929 B2 | 12/2008 | Nusser et al. |
| 7,472,939 B2 | 1/2009 | Tores |
| 7,731,675 B2 | 6/2010 | Aboul-Hosn et al. |
| 7,753,837 B2 | 7/2010 | Melvin |
| 7,927,068 B2 | 4/2011 | McBride et al. |
| 7,934,909 B2 | 5/2011 | Neusser et al. |
| 2002/0123661 A1 | 9/2002 | Verkerke et al. |
| 2003/0135086 A1 | 7/2003 | Khaw et al. |
| 2003/0231959 A1 | 12/2003 | Snider |
| 2004/0044266 A1 | 3/2004 | Siess et al. |
| 2004/0046466 A1 | 3/2004 | Siess et al. |
| 2004/0093074 A1 | 5/2004 | Hildebrand et al. |
| 2004/0215222 A1 | 10/2004 | Krivoruchko |
| 2004/0215228 A1 | 10/2004 | Simpson et al. |
| 2006/0008349 A1 | 1/2006 | Khaw |
| 2006/0062672 A1 | 3/2006 | McBride et al. |
| 2006/0195004 A1 | 8/2006 | Jarvik |
| 2008/0132747 A1 | 6/2008 | Shifflette |
| 2008/0236124 A1 | 10/2008 | Heinzelmann |
| 2008/0262584 A1 | 10/2008 | Bottomley et al. |
| 2008/0306327 A1 | 12/2008 | Shifflette |
| 2009/0060743 A1 | 3/2009 | McBride et al. |
| 2009/0093764 A1 | 4/2009 | Pfeffer et al. |
| 2009/0093796 A1 | 4/2009 | Pfeffer et al. |
| 2010/0041939 A1 | 2/2010 | Siess |
| 2010/0268017 A1 | 10/2010 | Siess |
| 2011/0238172 A1 | 9/2011 | Akdis |
| 2011/0275884 A1 | 11/2011 | Scheckel |
| 2012/0039711 A1 | 2/2012 | Roehn |
| 2012/0041254 A1 | 2/2012 | Scheckel |
| 2012/0046648 A1 | 2/2012 | Scheckel |
| 2012/0093628 A1 | 4/2012 | Liebing |
| 2012/0101455 A1 | 4/2012 | Liebing |
| 2012/0142994 A1 | 6/2012 | Toellner |
| 2012/0184803 A1 | 7/2012 | Simon et al. |
| 2012/0224970 A1 | 9/2012 | Schumacher et al. |
| 2012/0234411 A1 | 9/2012 | Scheckel |
| 2012/0237353 A1 | 9/2012 | Schumacher et al. |
| 2012/0237357 A1 | 9/2012 | Schumacher et al. |
| 2012/0264523 A1 | 10/2012 | Liebing |
| 2012/0265002 A1 | 10/2012 | Roehn et al. |
| 2012/0294727 A1 | 11/2012 | Roehn |
| 2012/0301318 A1 | 11/2012 | Er |
| 2012/0308406 A1 | 12/2012 | Schumacher |
| 2013/0019968 A1 | 1/2013 | Liebing |
| 2013/0041202 A1 | 2/2013 | Toellner |
| 2013/0060077 A1 | 3/2013 | Liebing |
| 2013/0066139 A1 | 3/2013 | Wiessler et al. |
| 2013/0085318 A1 | 4/2013 | Toellner |
| 2013/0177409 A1 | 7/2013 | Schumacher et al. |
| 2013/0177432 A1 | 7/2013 | Toellner |
| 2013/0204362 A1 | 8/2013 | Toellner |
| 2013/0237744 A1 | 9/2013 | Pfeffer et al. |
| 2014/0039465 A1 | 2/2014 | Schulz et al. |

FOREIGN PATENT DOCUMENTS

| | | |
|---|---|---|
| CA | 2701809 A1 | 4/2009 |
| CA | 2701810 | 4/2009 |
| CZ | 69427390 T2 | 9/2001 |
| DE | 350682 C | 3/1922 |
| DE | 2207296 A1 | 8/1972 |
| DE | 2113986 A1 | 9/1972 |
| DE | 2233293 A1 | 1/1973 |
| DE | 2613696 A1 | 10/1977 |
| DE | 4124299 A1 | 1/1992 |
| DE | 69103295 T2 | 12/1994 |
| DE | 19535781 A1 | 3/1997 |
| DE | 19541 549 A1 | 5/1997 |
| DE | 19971935 A1 | 4/1998 |
| DE | 69407869 T2 | 4/1998 |
| DE | 29804046 U1 | 6/1998 |
| DE | 69017784 T3 | 4/2000 |
| DE | 10059714 C1 | 5/2002 |
| DE | 10108810 A1 | 8/2002 |
| DE | 10155011 A1 | 5/2003 |

(56) References Cited

FOREIGN PATENT DOCUMENTS

| | | |
|---|---|---|
| DE | 69431204 T2 | 8/2003 |
| DE | 10336902 B3 | 8/2004 |
| DE | 103 24 717 A1 | 8/2005 |
| DE | 102010011998 A1 | 9/2010 |
| EH | 2366412 A2 | 9/2011 |
| EP | 0 415 333 A2 | 3/1991 |
| EP | 0480102 A1 | 4/1992 |
| EP | 0560000 A2 | 9/1993 |
| EP | 0629412 B1 | 1/1998 |
| EP | 0884064 A2 | 12/1998 |
| EP | 0916359 A1 | 5/1999 |
| EP | 1066851 A1 | 1/2001 |
| EP | 0914171 B1 | 10/2001 |
| EP | 0768091 B1 | 7/2003 |
| EP | 0951302 B1 | 9/2004 |
| EP | 1114648 B1 | 9/2005 |
| EP | 1019117 B1 | 11/2006 |
| EP | 1337288 B1 | 3/2008 |
| EP | 2218469 A1 | 8/2010 |
| EP | 2229965 A1 | 9/2010 |
| EP | 2301598 A1 | 3/2011 |
| EP | 2308524 A1 | 4/2011 |
| EP | 2343091 A1 | 7/2011 |
| EP | 2345440 A1 | 7/2011 |
| EP | 1651290 B1 | 1/2012 |
| EP | 2497521 A1 | 9/2012 |
| EP | 2606919 A1 | 6/2013 |
| EP | 2606920 A1 | 6/2013 |
| EP | 2607712 A1 | 6/2013 |
| GB | 2239675 A | 7/1991 |
| JP | 61-062614 A | 3/1986 |
| JP | 62-188610 U | 12/1987 |
| RU | 2229899 C2 | 6/2004 |
| WF | 2007103464 A2 | 9/2007 |
| WO | 9202263 A1 | 2/1992 |
| WO | 9302732 A1 | 2/1993 |
| WO | 9303786 A1 | 3/1993 |
| WO | 9314805 A1 | 8/1993 |
| WO | 9401148 A1 | 1/1994 |
| WO | 9405347 A1 | 3/1994 |
| WO | 9409835 A1 | 5/1994 |
| WO | 9420165 A2 | 9/1994 |
| WO | 9523000 A2 | 8/1995 |
| WO | 9618358 A1 | 6/1996 |
| WO | 9625969 A2 | 8/1996 |
| WO | 9744071 A1 | 11/1997 |
| WO | 9853864 A1 | 12/1998 |
| WO | 9919017 A1 | 4/1999 |
| WO | 0027446 A1 | 5/2000 |
| WO | 0043054 A2 | 7/2000 |
| WO | 0062842 | 10/2000 |
| WO | 0107760 A1 | 2/2001 |
| WO | 0107787 A1 | 2/2001 |
| WO | 0183016 A2 | 11/2001 |
| WO | 03057013 A2 | 7/2003 |
| WO | 03103745 A2 | 12/2003 |
| WO | 2005002646 A1 | 1/2005 |
| WO | 2005016416 A1 | 2/2005 |
| WO | 2005021078 A1 | 3/2005 |
| WO | 2005030316 A1 | 4/2005 |
| WO | 2005032620 A1 | 4/2005 |
| WO | 2005081681 A2 | 9/2005 |
| WO | 2006034158 A2 | 3/2006 |
| WO | 2006020942 A1 | 6/2006 |
| WO | 2006133209 A1 | 12/2006 |
| WO | 2007003351 A1 | 1/2007 |
| WO | 2007103390 A2 | 9/2007 |
| WO | 2007112033 A2 | 10/2007 |
| WO | 2008017289 A2 | 2/2008 |
| WO | 2008034068 A2 | 3/2008 |
| WO | 2008054699 A2 | 5/2008 |
| WO | 2008106103 A2 | 9/2008 |
| WO | 2008116765 A2 | 10/2008 |
| WO | 20080124696 A1 | 10/2008 |
| WO | 2008137352 A1 | 11/2008 |
| WO | 2008137353 A1 | 11/2008 |
| WO | 2009015784 A1 | 2/2009 |
| WO | 2010133567 A1 | 11/2010 |
| WO | 2013034547 A1 | 3/2013 |
| WO | 2013092971 A1 | 6/2013 |
| WO | 2013093001 A2 | 6/2013 |
| WO | 2013093058 A1 | 6/2013 |

\* cited by examiner

FLEXIBLE SHAFT ARRANGEMENT

BACKGROUND OF THE INVENTION

The invention is in the field of mechanical engineering, in particular mechanics, and relates to the transfer of torques and movements via flexible shafts. Flexible shaft drives are known from different fields of the art, with them varying greatly with respect to the torques to be transferred and the speeds. Shaft arrangements are, for example, known from the field of flexibly usable machine tools which run at relatively low speeds and should transfer high torques, whereas shafts are known from dental engineering which rotate at extremely high speeds and transfer lower torques.

Different problems result in the operation of such shafts, in particular as a consequence of the vibration behavior. Small asymmetries at certain points of a shaft arrangement and/or at certain speeds can result in knocking movements with corresponding unpleasant noise developments and in mechanically high strains due to friction between the shaft and its guidance.

Different proposals have become known on how to be able to reduce such knocking movements, for example from German patent No. 350682, in which the kinking of a sleeve of a flexible shaft at points is proposed to narrow the inner contour of the sleeve sectionally and thus to enforce a direct and clearance-free contact of the shaft in these regions, which is associated with a certain friction, but may result in a clearance-free guidance of the shaft and thus in the prevention of knocking movements.

DE 103 24 717 A1 discloses a ductile drive cable in which a core is surrounded by a circle of leads, with the leads having different cross-sections and an asymmetrical arrangement thereby arising within a jacket.

In accordance with JP 61 062614 A, a core is provided within a sleeve and in a jacket with the latter, with the sleeve and the jacket each extending in the same sense and coaxially to one another in changing arcs.

It is known from the laying-open publication DE 195 41 549 A1 to deform a sleeve, in which the shaft runs, selectively inwardly radially toward the shaft to fix the shaft sufficiently in the interior of the sleeve. It is moreover mentioned there that corresponding deformations can be offset helically section-wise. Squeezing, arching and compressing the sleeve is spoken of there.

BRIEF SUMMARY OF THE INVENTION

It is the underlying object of the present invention with respect to the prior art to provide a shaft arrangement which allows an operation of the shaft at high speeds with low friction and in so doing ensures that a minimum service life of the shaft arrangement can be guaranteed and that vibrations of the shaft can be reliably prevented. In this respect, the solution should in particular be able to be used with long and very thin shafts. Damage to or deformation of the shaft itself within the shaft arrangement must be able to be precluded.

The object is achieved in accordance with the invention by the features of claim 1.

In contrast to the known prior art, in accordance with the invention, a ductile shaft, a sleeve surrounding it and a jacket surrounding the sleeve and the shaft are provided for the shaft arrangement. The shaft should be able to rotate freely within the jacket, whereas the jacket is usually stationary.

Provision is made to achieve the object that the sleeve extends in arcuate form at least sectionally within the jacket. This means that the sleeve has a different spacing from a center axis, a longitudinal axis or a an axis of symmetry along the length of the jacket in some regions than in other regions or, in other words, differs sectionally along the length of the jacket, in particular in arcs, from the longitudinal axis, the axis of symmetry or the center line of the jacket, said axis not necessarily having to extend straight.

It is hereby achieved that the shaft which is arranged with clearance within the sleeve and which is rotatable relative thereto, contacts the inner wall of the sleeve section-wise inside the sleeve due to its inherent stiffness. A point-wise fixing of the shaft in a sliding friction relationship at the inner wall of the sleeve thereby results. Any vibrations of the shaft which occur are thus damped with minimal friction.

This solution has the advantage that the inner contour of the sleeve can remain very largely unchanged in cross-section so that the shaft has the necessary space for the rotation within the sleeve, for example in the form of a cylindrical inner space when the sleeve has a circular cross-section and a hollow-cylindrical shape. The arcuate shape of the sleeve has to be sufficiently pronounced for this purpose, which is, however, easy to effect in the individual application.

Provision is made that at least one spacer arrangement is provided at a part of the periphery between the inner contour of the jacket and the outer contour of the sleeve in at least one axially bounded section. In this respect, the jacket can extend substantially straight; this means that any arcs in which the jacket extends have substantially larger radii than the arcs which the sleeve describes within the jacket. Corresponding arc radii of the jacket can, for example, be at least 3 times, 5 times, 10 times or 50 times as large as the radii of the arc sections which are formed by the sleeve inside the jacket. As a rule, the sleeve is disposed with radial clearance within the jacket. This clearance is eliminated or at least reduced by the spacer device and the sleeve lies at the inner contour of the jacket on a side of the longitudinal axis eccentrically thereto. It is not necessary for this purpose that the corresponding spacer device does not extend in an azimuthal manner at the total periphery of the sleeve or of the jacket, but is rather only provided in a specific azimuthal peripheral section.

Provision is advantageously made that a plurality of spacer arrangements are provided spaced apart from one another along the length of the shaft arrangement. A wave-shape contour of the sleeve within the jacket is enforced by such an arrangement of the spacer device and can, for example, be meandering or of sinus wave shape.

Provision can moreover be made that directly mutually adjacent spacer arrangements are offset angle-wise with respect to one another azimuthally at the periphery of the shaft arrangement with respect to the shaft. A three-dimensional wave-shaped profile of the sleeve hereby results so that the shaft is fixed in a plurality of planes.

Provision can, for example, be made for this purpose that the spacer arrangements are arranged helically or circumferentially in the axial direction.

An advantageous realization of the invention provides that the spacer arrangement comprises at least one imprinting of the jacket radially inwardly or of the sleeve radially outwardly.

The material of the sleeve or of the jacket can be made so thin that imprints indent or bulge the respective contour, that is the inner contour of the jacket and/or the outer contour of the sleeve, such that an elevated portion is created by the imprinting which forms a corresponding spacer device.

Provision can be made in a particularly simple construction realization of the invention that the sleeve is made as a wound spiral. A simple type of manufacture of the sleeve is thus made possible and the cooling of the shaft within the sleeve is moreover facilitated by a free exchange of a coolant, for example a liquid, through the spiral within the jacket.

Such a spiral can advantageously comprise a flat material, for example in the form of a metal sheet or a plastic material. Provision can be made in this respect that the spacer arrangement is made as radially outwardly directed imprints of individual windings or groups of windings of the spiral. It is, however, also possible to use a round material and to provide it with corresponding imprints.

The advantage of such a construction comprises the fact that the material stretched before the winding of the spiral can be imprinted as such and that the corresponding imprints subsequently form the desired elevated portions on the winding of the spiral. This procedure facilitates the production, with the desired locations of the spacer devices/elevated portions being able to be predetermined by corresponding spacings of the imprints on the stretched spiral material. The imprints can in this respect in each case only be provided on individual winds of the windings or on mutually directly adjacent winds of the winding. In the forming of groups of imprints, the imprints of directly mutually adjacent windings of the spiral are disposed close to one another with respect to the periphery and the imprints of the respective next group can then be offset angle-wise with respect to the adjacent group.

Provision can, however, also be made that individual windings are imprinted at certain axial intervals from one another in a helically circumferential arrangement.

Provision can moreover advantageously be made that the imprints or groups of imprints are arranged equidistantly from one another with respect to the spiral material stretched before the winding. It can be ensured by a correspondingly calculated spacing of the imprints on the starting material of the spiral that the angle-wise offset of mutually following elevated portions/spacer devices will also be regular.

In addition to a flexible shaft arrangement in accordance with the above description, the invention also relates to a method for manufacturing such a shaft arrangement in which a spiral material is imprinted before the winding to a spiral forming the sleeve such that at least one elevated portion arises which is radially outwardly directed with respect to the sleeve.

A manufacturing process of this type is, on the one hand, easy to carry out and, on the other hand, allows the precise predetermination of the corresponding spacer devices to ensure the optimized extent of the sleeve within the jacket for a problem-free operation of the shaft.

Finally, the invention also relates to a blood pump arrangement having a flexible shaft arrangement such as is described above in different embodiments. Such blood pump arrangements can, for example, be introduced in a minimally invasive process through a blood vessel into the body of a patient to assist or to replace heart activity. The shaft then represents the drive shaft of a pump rotor and rotates with speeds of typically more than 10,000 r.p.m. It is connected to a rotor of the pump, for example to a rigid shaft of the rotor or, with a hubless rotor, to one of its end faces. The shaft can also merge in one piece into a rotor shaft and can bear one or more impeller blades at its pump-side end. The sleeve and the jacket then end in front of the rotor.

BRIEF DESCRIPTION OF THE DRAWINGS

The invention will be shown and subsequently described in the following with reference to an embodiment in a drawing.

There are shown

DETAILED DESCRIPTION OF THE INVENTION

Figure 1:
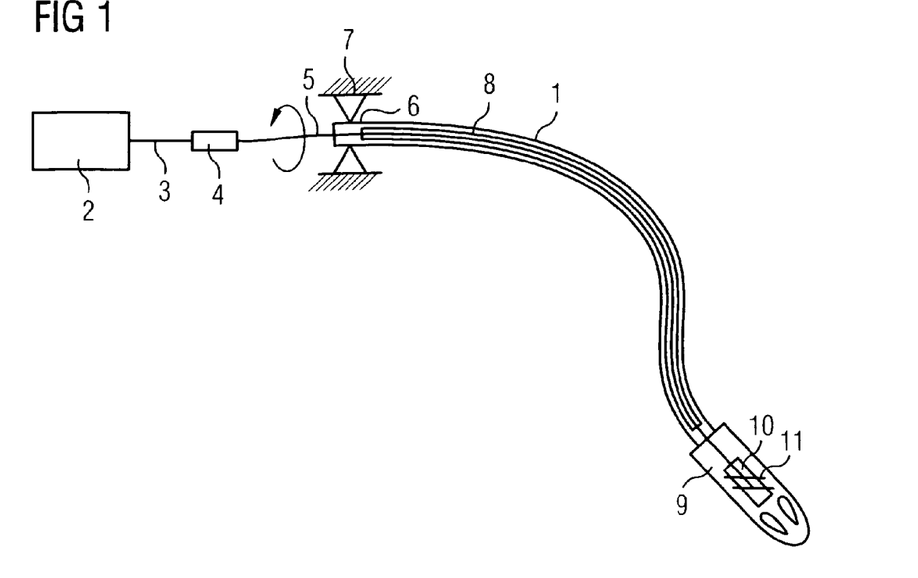
FIG. 1 schematically, a flexible shaft arrangement having a drive and a unit driven by means of the shaft.

FIG. 1 shows the shaft arrangement 1 in a schematic view with a motor drive which has an electric motor 2 as well as a motor shaft 3 and a coupling 4 by means of which the flexible shaft 5 is rotationally fixedly coupled to the motor 2. In addition, a jacket 6 of the shaft arrangement is shown which is fixed in the holder 7 at the motor side. A sleeve 8 which surrounds the shaft 5 is shown in the interior of the jacket.

A pump 9 having a pump rotor 10 which has impeller blades 11 is shown on the output side of the shaft arrangement. Such a pump can serve in medical engineering in the microinvasive sector, for example, for conveying blood in a blood vessel and forms a very fast-rotating axial flow pump.

The shaft arrangement in accordance with the invention solves the problem that the very fast-rotating shaft 5, i.e. rotating at more than ten thousand revolutions per minute, can be prone to knocking movements which can result in disturbing noise development and in some cases also to a point-wise increased wear so that the service life of the shaft arrangement is impaired.

Figure 2:
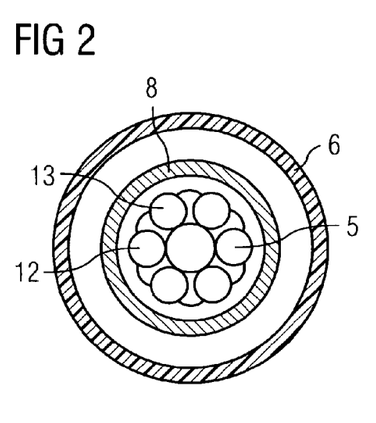
FIG. 2 a shaft arrangement in accordance with the invention in a first cross-section.

The cross-section of the shaft arrangement in which the jacket 6 is shown at the outside will first be looked at for the solution of the problem. Said jacket can, for example, be made as a plastic jacket or also as a thin-walled metal jacket. The sleeve 8, which can likewise be made of metal or of plastic, is located within the jacket 6. Clearance is provided between the jacket 6 and the sleeve 8 since the sleeve 8 can optionally move with the shaft 6 within the jacket.

The shaft 5 comprises a plurality of braided strands 12, 13 to produce the corresponding flexibility. Clearance is likewise provided between the shaft 5 and the sleeve 8 to minimize the friction.

Figure 3:
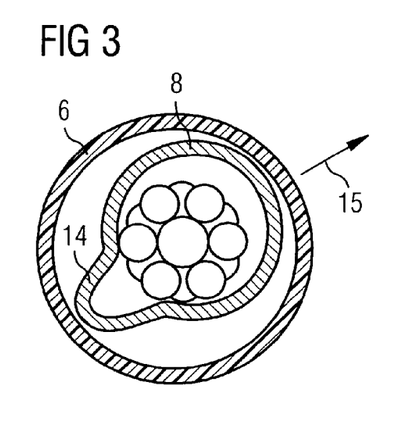
FIG. 3 a shaft arrangement in accordance with the invention in a second cross-section.

FIG. 3 shows a cross-section at a point of the shaft arrangement at which a spacer device is provided between the sleeve 8 and the jacket 6. The spacer device 14 is made as a radially outwardly directed elevated portion in the sleeve 8. The sleeve 8 is urged in cross-section in the direction of the arrow 15 within the inner contour of the jacket 6 by this elevated portion.

Since the elevated portion 14 is only provided in a closely bounded section of the shaft arrangement in the axial direction, as will be explained in more detail further below, this deflection of the sleeve 8 only takes place axially point-wise within the jacket 6 so that the sleeve 8 adopts a wave shape within the jacket 6. The elevated portion 14 can be produced, for example, by an imprint in the material of the sleeve 8 from the inside radially to the outside.

The shaft is formed, for example by twisting from thin threads/wires, with each individual strand element of the shaft having a diameter which is between half and twice the height of the elevated portion in the sleeve. A snagging of shaft elements with the irregularities/imprints of the sleeve is thus avoided.

It is also advantageous, for example, in a modification for avoiding the snagging of the shaft elements in the irregularities/imprints of the sleeve if the imprints are formed or are arranged in a different pitch around the sleeve than that in which the shaft elements of the shaft are wound so that no parallelism is present between the shaft elements and the irregularities/imprints.

Figure 4:
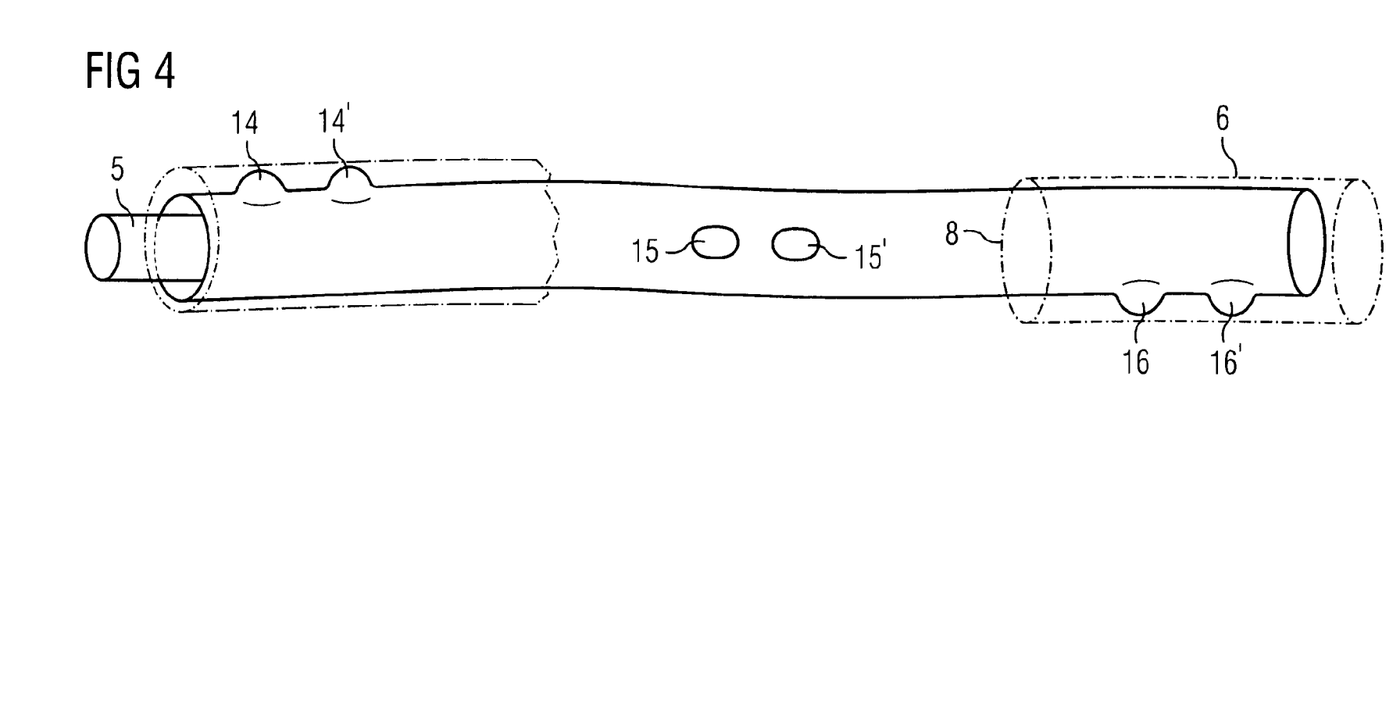
FIG. 4 the sleeve of the shaft arrangement in accordance with the invention with a shaft in a three-dimensional view.

FIG. 4 shows in a three-dimensional view a plurality of elevated portions 14, 14', 15, 15', 16, 16', wherein the groups of elevated portions are each axially spaced apart from one another and are mutually displaced azimuthally angle-wise with respect to the longitudinal axis of the shaft arrangement. The position of the groups of elevated portions changes in helical form in the clockwise direction running from left to right. If the sleeve shown is imagined as located in an elongated jacket 6 (shown by dashed lines), the sleeve is displaced, as is shown in FIG. 4, with respect to the jacket axis in the region of the elevated portions 14, 14' downwardly in the region of the elevated portions 15, 15' to the rear into the plane of the drawing and upwardly in the region of the elevated portions 16, 16'.

A wave shape of the sleeve 8 thus results when the jacket is considered as stable in shape. This has the result that the shaft 5, which has the tendency due to its inherent stiffness to run straight without any external effect, contacts in each case the inner contour of the sleeve 8 in the region of the elevated portions. The shaft 5 is thus sufficiently fixed in order to damp a large part of the knocking movements via friction.

Figure 5:
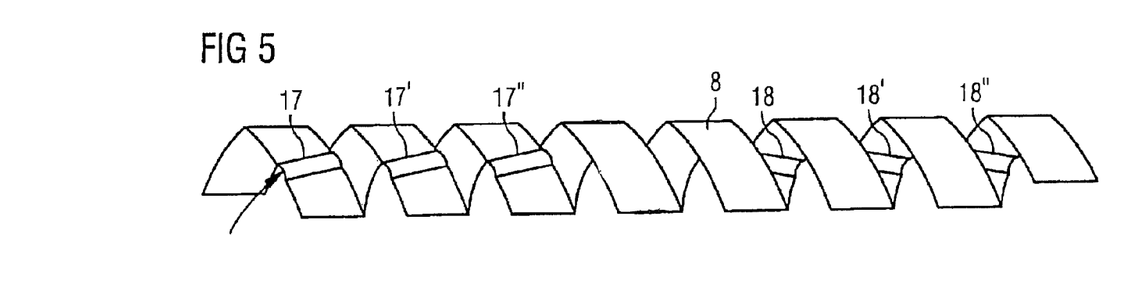
FIG. 5 a sleeve in accordance with the invention in a three-dimensional view.

FIG. 5 shows in a three-dimensional representation only a sleeve 8 which is made as a spiral in the embodiment shown. The spiral has elevated portions 17, 17', 17" and 18, 18', 18" which are mutually offset axially and in the peripheral direction. In the example shown, the elevated portions are mutually displaced by 180 degrees at the periphery.

Figure 6:
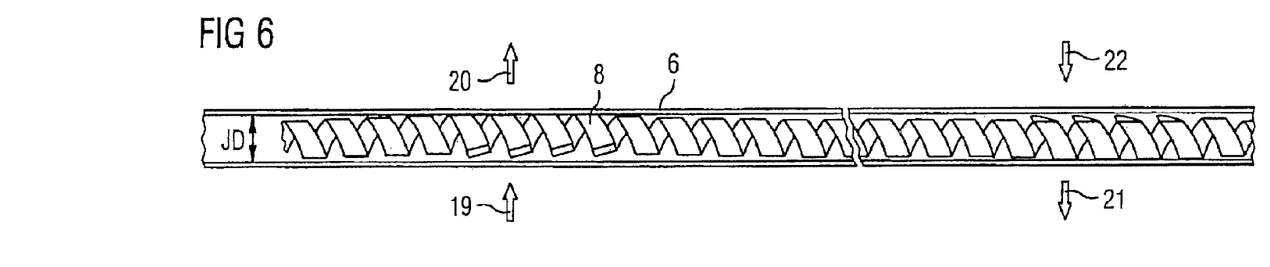
FIG. 6 a sleeve in accordance with the invention in a jacket in a longitudinal section.

The manner is shown in FIG. 6 in which the shown spiral in a jacket 6 contacts its inner contour. It is shown that in the region 19, in which the imprints are provided below the center axis, the sleeve 8 is displaced upwardly in the direction of the arrow 20, whereas the sleeve is displaced downwardly in the direction of the arrow 22 in the region 21 due to the imprints located above the center axis there. The addressed wave shape of the sleeve 8 thus results.

Figure 7:
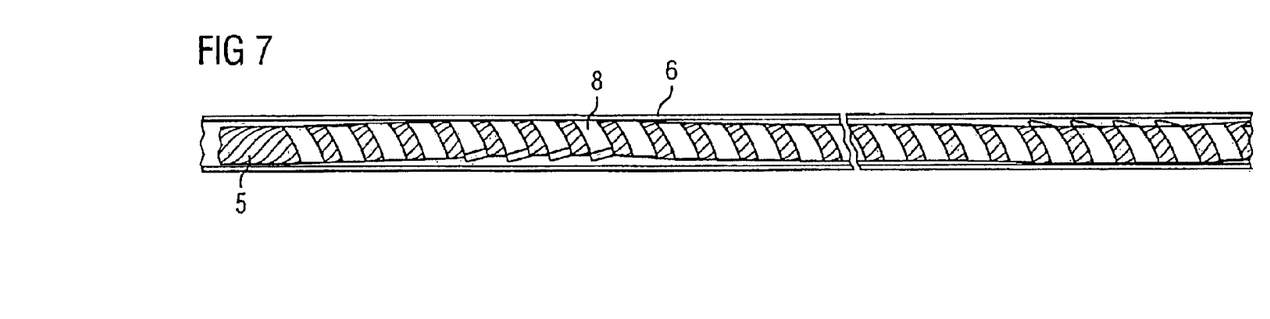
FIG. 7 a shaft arrangement having a shaft, a sleeve and a jacket in accordance with the invention in a longitudinal section.

In FIG. 7, the Figure is further completed in that a shaft 5 is also drawn in which is conducted within the circular contour of the sleeve. The sleeve 8 is shown in the wave shape already introduced in FIG. 6 and the shaft 5 contacts at least spot-wise the inner contour of the sleeve 8 under sliding friction conditions.

The invention can thus be used beneficially in the sector of medical engineering where very fast-rotating shafts are required within a hollow catheter in a body, for example. The hollow catheter can also take over the role of the jacket. The total shaft arrangement can, however, also be arranged within a hollow catheter.

A reduction in friction, in wear and in noise development takes place with a design of the shaft arrangement in accordance with the invention. This also has the result, for example, that a reduced torque is required to drive the shaft, which is in particular useful on use of complex sluices for leading through the shaft from the body exterior to the body interior.

Figure 8:
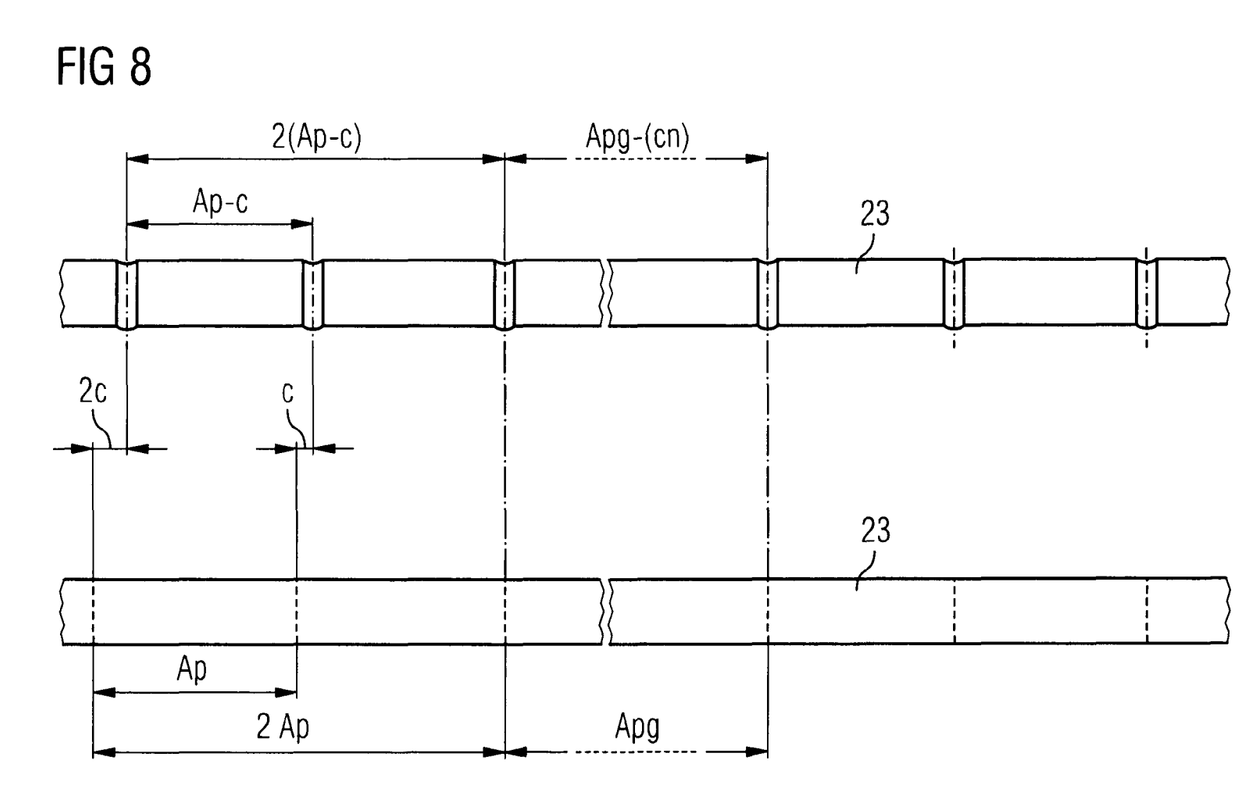
FIG. 8 a distribution scheme of the imprints on the flat material from which the sleeve is later wound.

FIG. 8 shows a scheme which is useful in the calculation of the spacings of the imprints in the starting material of the spiral. The strand material of the spiral is labeled by 23 in the Figure. In the upper region of FIG. 8, the strand is shown before the introduction of imprints; in the lower region after the introduction of the imprints. In this respect, the spacing of the imprints within an imprint group is labeled by Ap. This results from an approximation equation for the ellipse calculation, wherein the amount by which the length is changed by the imprinting is taken into account. The spacing Ap of two adjacent imprints results from the formula $$AP \approx \left[(a+b)\cdot\pi\cdot\left\{1 + \frac{3\lambda^2}{10 + \sqrt{4-3\lambda^2}}\right\}\right] + c,$$

where $$\lambda = \frac{a-b}{a+b}$$

is given. a designates the large semicircle, b the small semicircle of the ellipse which is given by the contour of a wind of the spiral observed in cross-section. The amount c results from the extension of the imprint spacing by the stretching of the material as a consequence of the imprint.

Provision can also be made that the parameter c±x is used instead of the parameter c to offset the imprints of adjacent winds at the periphery by a constant angle with respect to one another and thus to achieve the helical circumferential distribution of the imprinted points.

The invention claimed is:

1. A flexible shaft arrangement, comprising:
a ductile rotating shaft,
a non-rotating sleeve surrounding said ductile shaft and,
a jacket surrounding the shaft and the sleeve, wherein the sleeve extends within the jacket along its length at least sectionally in arcuate shape differing from the longitudinal axis, axis of symmetry or center line of the jacket, and wherein the sleeve can move within the jacket, and wherein a plurality of individual spacers are formed of said sleeve in the radially outward direction, wherein directly mutually adjacent individual spacers are mutually offset angle-wise azimuthally about said sleeve from one another and are mutually axially spaced apart along the length of the sleeve from one another.

2. The flexible shaft arrangement in accordance with claim 1, wherein directly mutually adjacent spacer arrangements are mutually offset angle-wise azimuthally at the periphery of the shaft arrangement with respect to the shaft.

3. The flexible shaft arrangement in accordance with claim 2, wherein the spacer arrangements are arranged spirally circumferentially in the axial direction.

4. The flexible shaft arrangement in accordance with claim 1, wherein the sleeve is made as a wound spiral.

5. The flexible shaft arrangement in accordance with claim 4, wherein the spiral comprises a substantially flat material.

6. The flexible shaft arrangement in accordance with claim 5, wherein the spacers are made as radially outwardly directed imprints of individual winds or groups of winds of the spiral.

7. The flexible shaft arrangement in accordance with claim 6, wherein the imprints or groups of imprints are arranged mutually equidistant before the winding of the stretched spiral material.

8. A method for manufacturing a shaft arrangement in accordance with claim 7, wherein a spiral material is imprinted before the winding into a spiral forming the sleeve so that at least one elevated portion arises which is radially outwardly directed with respect to the sleeve.

9. A flexible shaft arrangement in accordance with claim 1, wherein said shaft is connected to a pump rotor for a blood pump.

10. The flexible shaft arrangement in accordance with claim 1, wherein said rotating shaft rotates at more than 10,000 rpm.

11. The flexible shaft arrangement in accordance with claim 1, wherein an inner contour of said sleeve is constant except at said spacers.

12. A flexible shaft arrangement, comprising:
a ductile rotating shaft,
a non-rotating sleeve surrounding said ductile shaft and,
a jacket surrounding the shaft and the sleeve, wherein the sleeve extends within the jacket along its length at least sectionally in arcuate shape differing from the longitudinal axis, axis of symmetry or center line of the jacket, and wherein the sleeve can move within the jacket, and wherein a plurality of individual spacers are formed of said sleeve and are mutually axially spaced apart along the length of the sleeve from one another.

13. A flexible shaft arrangement, comprising:
a ductile rotating shaft,
a non-rotating sleeve surrounding said ductile shaft and,
a jacket surrounding the shaft and the sleeve, wherein the sleeve extends within the jacket along its length at least sectionally in arcuate shape differing from the longitudinal axis, axis of symmetry or center line of the jacket, and wherein the sleeve can move within the jacket, and wherein a plurality of individual spacers are formed of said sleeve in the radially outward direction and are mutually axially spaced apart along the length of the sleeve from one another.

* * * * *